Figure 1:
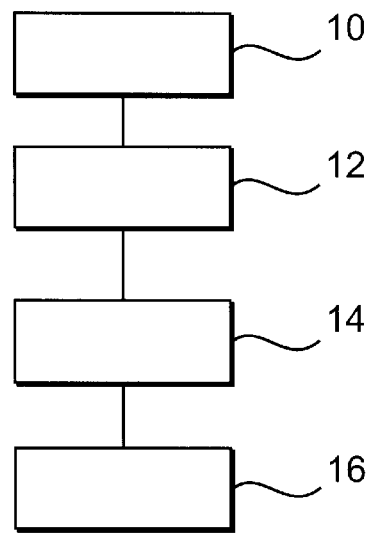

United States Patent
Berger

[11] Patent Number: 5,904,816
[45] Date of Patent: May 18, 1999

[54] PROCESS FOR THE CHEMICAL MODIFICATION OF LIQUIDS CONTAINING ALKYL GROUPS

[75] Inventor: Steffen Berger, Düsseldorf, Germany

[73] Assignee: Arplas Gesellschaft Für Plasmatechnologie mbH, Weissandt-Gölzau, Germany

[21] Appl. No.: 08/836,711

[22] PCT Filed: Nov. 23, 1995

[86] PCT No.: PCT/EP95/04620

§ 371 Date: May 13, 1997

§ 102(e) Date: May 13, 1997

[87] PCT Pub. No.: WO96/15852

PCT Pub. Date: May 30, 1996

[30] Foreign Application Priority Data

Nov. 24, 1994 [DE] Germany .............. 44 43 239

[51] Int. Cl.⁶ ............................................. H05F 3/00
[52] U.S. Cl. ................ 204/157.15; 204/164; 204/165
[58] Field of Search ........................... 204/164–169, 204/172, 157.15

[56] References Cited

U.S. PATENT DOCUMENTS 5,549,795  8/1996  Gregoire et al. ............... 204/168

FOREIGN PATENT DOCUMENTS

| 0 122 289 | 10/1984 | European Pat. Off. . |
| 0 593 988 A1 | 4/1994 | European Pat. Off. . |
| 41 41 805 A1 | 6/1993 | Germany . |
| 61-069804 | 4/1986 | Japan . |
| 1 326 197 | 8/1973 | United Kingdom . |
| WO 91/08047 | 6/1991 | WIPO . |
| WO 94/03263 | 2/1994 | WIPO . |
| WO 95/03344 | 2/1995 | WIPO . |

OTHER PUBLICATIONS

Chemical Abstracts, 26473d., vol. 81, No. 6, Aug. 12, 1974.

Kunststoff Taschenbuch, 25th Edition, pp. 258–259 (No Date Available).

*Primary Examiner*—Kishor Mayekar
*Attorney, Agent, or Firm*—Finnegan, Henderson, Farabow, Garrett & Dunner, L.L.P.

[57] ABSTRACT

The invention relates to a process for the chemical modification of liquids containing alkyl groups. It is provided that the liquids containing alkyl groups are subjected to a plasma treatment in a frequency range from 10 kHz to 10 GHz.

11 Claims, 1 Drawing Sheet

PROCESS FOR THE CHEMICAL MODIFICATION OF LIQUIDS CONTAINING ALKYL GROUPS

This application is a 35 U.S.C. 371 National Stage Filing of PCT/EP95/04620, filed on Nov. 23, 1995.

The invention relates to a process for the chemical modification of liquids containing alkyl groups, and to chemically modified liquids containing alkyl groups.

It is known that liquids containing alkyl groups, for example alkylsulfanates [sic], fatty acids, fatty alcohols and their processing products, can be used in many areas. Use is possible, for example, in emulsions and dispersions For the processability of the liquids containing alkyl groups in the most varied areas of use, these liquids must be mixed with certain additives matched to the particular area of use. Owing to the great many possible fields of application, comprehensive uniform use of the liquids containing alkyl groups is thus impossible.

Kunststoff-Taschenbuch [Plastics Handbook], 25th edition, pages 248 to 259, discloses a process for the aftertreatment of solids containing alkyl groups. In this case the surface of the solid containing alkyl groups, for example a PE surface, is treated with a high-voltage plasma, in order to achieve local chemical modification. Owing to this local surface treatment, for example in the case of shaped components, an improvement of the coatability or printability is achieved. However, it is a disadvantage in this case that an additional aftertreatment must be performed whose use is possible only to a restricted extent owing to the provision of a high-voltage plasma unit for the finished product.

The object therefore underlying the invention is to create a process of the generic type by which a chemical modification of liquids containing alkyl groups is possible in a simple and inexpensive manner.

According to the invention, this object is achieved by means of the fact that the liquids containing alkyl groups are subjected to a plasma treatment in a frequency range from 10 kHz to 10 GHz. It has surprisingly been found that a modification of material properties can be induced within the liquids containing alkyl groups by means of the plasma treatment. In particular, by means of the plasma treatment of the liquid containing alkyl groups, special chemical products can be achieved which can be used in a varied manner without needing a chemical aftertreatment. By means of the plasma treatment, a high level of chemical modification in terms of quality and quantity can be achieved. A degree of the chemical modification of the liquids containing alkyl groups may preferably be achieved in a simple manner by setting parameters of the plasma treatment.

In an advantageous development of the invention it is provided that the plasma treatment is carried out with alternating frequencies, preferably with combinations of different alternating frequencies. Thus, the plasma treatment can highly advantageously be carried out with successively selectable frequencies, with alternately selectable different frequencies, with at least two simultaneously selectable different frequencies, and combinations of frequency selections resulting herefrom. By this means, the chemical modification can be highly advantageously matched to the variable chemical structure of the liquids containing alkyl groups used and to their application following the chemical modification.

In a further advantageous development of the invention, it is provided that the plasma treatment is carried out with supply of at least one inert gas, for example helium and/or argon and/or with supply of at least one reaction gas, for example oxygen and/or nitrogen. It is further preferred if the plasma treatment is carried out successively with an inert gas plasma and at least one reaction gas plasma and/or a reaction gas plasma mixture or with supply of a mixture of at least one inert gas and one reaction gas. By choosing a process gas composition during the plasma treatment (inert gas, reaction gas, reaction gas mixture) which is matched to the liquids containing alkyl groups which are to be modified, it is possible to incorporate the reactive groups which are necessary for the chemical modification, for example hydroxyl groups, carboxyl groups, primary and secondary amino groups, into the liquids containing alkyl groups to a sufficient extent. These incorporated groups are able to react with the liquid containing alkyl groups and to enter into chemical bonds and/or to adhere physically. Further polar, but unreactive, groups which can be incorporated, for example carbonyl groups, tertiary amino groups, can likewise effect a change in properties of the liquid containing alkyl groups. In the plasma treatment, a relatively homogeneous modification of the liquids containing alkyl groups with the reactive or unreactive groups incorporated during the plasma treatment is possible.

The modified liquid containing alkyl groups after the plasma treatment thus has a relatively homogeneous distribution of the reactive or unreactive incorporated groups over the entire spatial extent of the liquid containing alkyl groups. Thus, any type of liquids containing alkyl groups can be achieved which are suitable for specific applications after the plasma treatment, a further subsequent treatment no longer being necessary. The liquids containing alkyl groups can be adjusted to their special application in a simple manner by the plasma treatment according to the invention.

In a further advantageous development of the invention, it is provided that solid and/or liquid reactants, auxiliaries and additives are added to the liquids containing alkyl groups prior to the plasma treatment. Owing to this optional admixture of the reactants or substances mentioned, the chemical modification of the liquids containing alkyl groups can be precisely matched to a specific application.

Further advantageous developments result from the remaining features mentioned in the subclaims.

Figure 2:
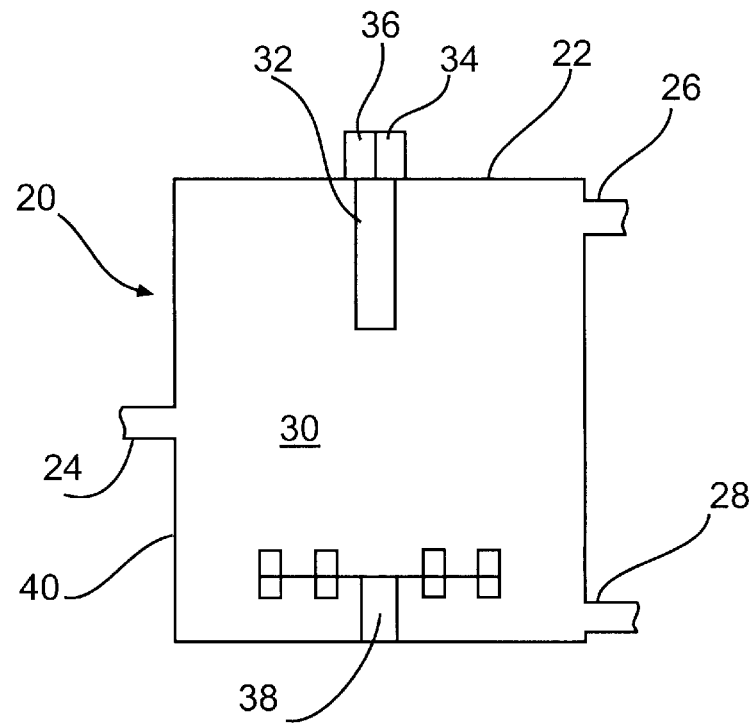

The invention is described below in more detail in illustrative examples with reference to the associated drawings. In the drawings:

FIG. 1 shows a process sequence for the chemical modification of a liquid containing alkyl groups and FIG. 2 shows a diagrammatic representation of an arrangement for carrying out the process.

In FIG. 1, the process according to the invention is intended to be explained with the aid of a diagram. In a first step, liquids containing alkyl groups available as starting materials are prepared. During the process step 10, reactants, auxiliaries and/or additives can be added to the liquids containing alkyl groups. In addition blending of different liquids containing alkyl groups is possible.

In a next step 12, the process parameters and process gases desired for the plasma treatment are set. In this case, in particular the special combinations of the process gases, that is a first treatment with an inert gas plasma, preferably with helium and/or argon, and the subsequent treatment with a reaction gas plasma, preferably with oxygen and/or nitrogen, or else the treatment with a plasma which is generated from a mixture of the abovementioned gases, are established. In addition, the high frequencies necessary for the plasma generation in vacuum and their time sequence are set. Thus, variants are conceivable in which a plasma treatment is carried out, firstly with a lower frequency, for example 13.56 MHz, and then with a higher frequency, for example 2.45 GHz. In addition, alternate addition of the process gases, that is of the inert gas, of the reaction gas and/or of a mixture of a reaction gas and an inert gas, is possible. Furthermore, an alternating, or if appropriate simultaneous, selection of different frequencies can be preset. Furthermore, the desired process pressure is set, which is, for example, in the range between 0.1 mbar and 2 mbar. During the plasma treatment, the process pressure can be subject to process-specific fluctuations. Furthermore, the treatment duration for which the plasma treatment is performed is specified. This is, for example, between 5 seconds and 15,000 seconds. Said process parameters or process gases can be varied in a combination among one another and are matched, in particular, to the composition of the respective liquids containing alkyl groups specifically present.

In a next process step 14, the plasma treatment of the liquids containing alkyl groups is then carried out using the process parameters and process conditions set in process step 12. In this case it is conceivable that during the plasma treatment the process parameters can be changed and/or adapted, for example by a controller. In addition, during the process step 14, the liquid can be mixed or stirred. By this means, a more homogeneous mixing with the reactive or unreactive groups incorporated via the plasma treatment is possible. Furthermore, the temperature of the liquid can be controlled during the plasma treatment. By targeted temperature control of the liquid it is also possible to change the viscosity during the plasma treatment, for example to increase or to decrease it, in order to influence in this manner the incorporation of the reactive or unreactive groups via the plasma treatment.

In a next process step 16, the liquid is further processed. This further processing can comprise, for example, compounding, spraying, coating drying etc. However, in the context of the present description, details of further processing of the modified melt will not be considered in more detail.

FIG. 2 shows diagrammatically a unit for the chemical modification of liquids containing alkyl groups. The unit is designated in general by 20 and is shown greatly simplified. The unit 20 possesses a reactor 22 which has at least one inlet port 24 for the liquids containing alkyl groups which are to be modified. The inlet port 24 can also be used for the addition of the reactants auxiliaries and/or additives In addition, the reactor 22 possesses an inlet port 26 for process gases or plasmas. The inlet port 26 can possess a plurality of part-inlets, which are not shown here, through which either an inert gas, a reaction gas and/or a mixture of an inert gas and a reaction gas or corresponding plasmas can be conducted in the reactor 22. Furthermore, the reactor 22 possesses an outlet 28 for the treated liquids containing alkyl groups. The reactor 22 can be hermetically sealed, so that a vacuum can be generated in an interior 30 of the reactor 22, with details not being considered further here. An electrode 32 protects into the interior 30, which electrode is coupled to a generator 34 for the microwave plasma excitation and to a high frequency feed 36. The electrode 32 can comprise a plurality of part-electrodes, in which case one can be designed for the microwave plasma excitation and one for the high-frequency feed. The shape of the electrode 32 can be, for example, rod-shaped, spherical, half-shell-shaped, etc. In addition, an agitator 38 is arranged in the interior 30. The agitator 38 is present only optionally, so that its presence is not required for the chemical modification according to the invention. Furthermore, the reactor 22 can be heatable, either via its outer jacket 40 or via the agitator 38 which can have appropriate heating elements.

The arrangement 20 shown here is only an example and can be replaced by any other suitable arrangement for carrying out the process according to the invention.

The unit 20 shown in FIG. 2 performs the following function:

The reactor 22 is charged with the liquid containing alkyl groups via the inlet port 24. Then, a plasma treatment of the liquid is carried out by means of the electrode 32 with simultaneous supply of a process gas via the inlet port 26. The electrode 32 in this case can alternately be excited with different frequencies. For this purpose it is alternately coupled to the generator 34 or the high-frequency feed 36. If appropriate, two electrodes 32 are present, one of the respective electrodes being coupled to the generator 34 and the other to the high-frequency feed 32. These can now be selected alternately. The process gas supplied via the intake port 26 leads in a known manner to the formation of a plasma within the interior 30 of the reactor 22. Depending on the composition of the process gas, a variable plasma is generated. In this case, via the inlet port 26, either an inert gas, a reaction gas or mixture of an inert gas and a reaction gas or a corresponding plasma can be supplied to the reactor 22. The inlet port 26 is designed in such a manner that the supply of the inert gas and/or of the reaction gas and/or of the mixture of the inert gas and reaction gas or of the corresponding plasma can be varied during the plasma treatment via control devices which are not to be considered here in more details That is to say, for different periods, different amounts of the process gas or plasma required in each case can be fed to the reactor 22.

After completion of the plasma treatment of the liquid, it is removed from the reactor 22 via the outlet port 28. The liquid exiting from the outlet port 28 can then be fed to a further processing or treatment. However, in the context of the present description, this possibility will not be considered further.

According to a further process variant, the liquid containing alkyl groups can be charged separately to a container which is then introduced into the reactor 22 through a suitable inlet port. After plasma treatment of the liquid has been carried out, this container can in turn be removed from the reactor 22, so that the inlet port 24 and the outlet port 28 can be dispensed with. By means of this variant, the structure of the reactor 22 can be optimized solely for the generation of the plasma.

According to a further procedure, it is conceivable to operate the reactor 22 on the continuous flow principle. That is to say, liquids containing alkyl groups are continuously supplied via the inlet port 24. The liquid is subjected to the plasma treatment within a section of the reactor 22 designed for the plasma treatment and is then withdrawn via the outlet port 28.

The different process variants described here for the plasma treatment of a liquid containing alkyl groups are only examples. It must be made clear that the specific structure of a unit 20 for carrying out the process according to the invention can be highly varied. The critical factor is that the liquids containing alkyl groups are subjected to a plasma treatment.

I claim:

1. Process for the chemical modification of liquids containing alkyl groups comprising subjecting the liquids containing alkyl groups to a plasma treatment in a frequency range from 10 kHz to 10 GHz, wherein the plasma treatment is carried out with alternating frequencies.

2. Process according to claim 1 wherein the plasma treatment is carried out with combinations of different alternating frequencies.

3. Process according to claim 1 wherein the plasma treatment is carried out in the presence of at least one inert gas.

4. Process according to claim 1 wherein the plasma treatment is carried out in the presence of at least one reaction gas.

5. Process according to claim 1 wherein the plasma treatment is fed successively with at least one inert gas plasma, at least one reaction gas plasma or a reaction gas mixture plasma or with a mixture of at least one inert gas and at least one reaction gas.

6. Process according to claim 1 wherein the plasma treatment is conducted in the presence of at least one inert gas plasma, at least one reaction gas plasma or at least one mixture of an inert gas/reaction gas plasma.

7. Process according to claim 1 wherein before and/or during and/or after the plasma treatment, solid and/or liquid reactants, auxiliaries and additives are added to the liquids containing alkyl groups.

8. Process according to claim 1 further comprising carrying out compounding before and/or during and/or after the plasma treatment.

9. Process according to claim 1 wherein the plasma treatment is performed at a process pressure of 0.1 mbar to 2 mbar.

10. Process according to claim 1 wherein the duration of the plasma treatment is between 5 seconds and 15,000 seconds.

11. Process according to claim 1 wherein the liquids containing alkyl groups are mixed/stirred during the plasma treatment.

* * * * *